US010529140B1

(12) United States Patent
Ravindran et al.

(10) Patent No.: US 10,529,140 B1
(45) Date of Patent: Jan. 7, 2020

(54) METHODS AND SYSTEMS FOR TREATING AUTISM

(71) Applicant: FLOREO, INC., Washington, DC (US)

(72) Inventors: Vijay Ravindran, Washington, DC (US); Vibha Sazawal, Washington, DC (US); Ali Moeeny, Baltimore, MD (US); Rita Solorzano, Washington, DC (US); Sinan Turnacioglu, Bethesda, MD (US)

(73) Assignee: FLOREO, INC., Washington, DC (US)

( * ) Notice: Subject to any disclaimer, the term of this patent is extended or adjusted under 35 U.S.C. 154(b) by 0 days.

(21) Appl. No.: 16/387,885

(22) Filed: Apr. 18, 2019

Related U.S. Application Data

(63) Continuation of application No. 15/782,216, filed on Oct. 12, 2017, now Pat. No. 10,311,645.

(60) Provisional application No. 62/408,663, filed on Oct. 14, 2016.

(51) Int. Cl.
| | |
|---|---|
| *G06T 19/00* | (2011.01) |
| *A61B 5/00* | (2006.01) |
| *A61N 1/36* | (2006.01) |
| *G02B 27/01* | (2006.01) |
| *G06F 3/01* | (2006.01) |
| *G06K 9/00* | (2006.01) |
| *A61M 21/00* | (2006.01) |

(52) U.S. Cl.
CPC ............ *G06T 19/006* (2013.01); *A61B 5/742* (2013.01); *A61N 1/36025* (2013.01); *G02B 27/0101* (2013.01); *G06F 3/011* (2013.01); *A61M 2021/005* (2013.01); *G01N 2800/28* (2013.01); *G02B 2027/0178* (2013.01); *G06K 9/00671* (2013.01)

(58) Field of Classification Search
None
See application file for complete search history.

(56) References Cited

U.S. PATENT DOCUMENTS

| | | | |
|---|---|---|---|
| 6,162,189 A | 12/2000 | Girone et al. | |
| 10,311,645 B1 | 6/2019 | Ravindran et al. | |
| 2013/0127980 A1 | 5/2013 | Haddick et al. | |
| 2016/0249989 A1 | 9/2016 | Devam et al. | |

OTHER PUBLICATIONS

Escobedo et al. Using Augmented Reality to Help Children with Autism Stay Focused. IEEE Pervasive Computing. Published: Feb. 28, 2014. pp. 38-46.
U.S. Appl. No. 15/782,216 Office Action dated Feb. 8, 2019.
U.S. Appl. No. 15/782,216 Notice of Allowance dated Feb. 27, 2019.
U.S. Appl. No. 15/782,216 Office Action dated Oct. 3, 2018.

*Primary Examiner* — Robert J Craddock
(74) *Attorney, Agent, or Firm* — Wilson, Sonsini, Goodrich & Rosati

(57) ABSTRACT

A method for treating autism is provided. The method includes presenting to affected subjects therapeutic content in the form of images or video in a virtual or augmented reality system and monitoring in real time the behaviors and responses of the subject to the therapy. The virtual or augmented reality system may further include audio, and the monitoring of the therapy may be achieved using one or more tracking sensors, such as a camera.

20 Claims, 12 Drawing Sheets

METHODS AND SYSTEMS FOR TREATING AUTISM

CROSS-REFERENCE

This application is a continuation of U.S. patent application Ser. No. 15/782,216, filed Oct. 12, 2017, which claims the benefit of U.S. Provisional Application No. 62/408,663, filed Oct. 14, 2016, each of which applications are entirely incorporated herein by reference.

BACKGROUND

Autism, also known as autism spectrum disorder (ASD), refers to a complex neurodevelopmental disorder in which affected subjects commonly show difficulties engaging in social interactions and communication and repetitive behaviors. Autism may affect millions of people in the United States alone, and is becoming more prevalent in the population every year. Although there is no known cure, today, autism therapy ranges across a myriad of specialties including neurology, psychiatry, physical therapy, occupational therapy, behavioral therapy, and speech language pathology. Such therapeutic methods can help autistic individuals gain social and communication skills.

Virtual or augmented reality is the coordinated experience of a user in an environment manufactured by and housed in computer processors and memory, where the environment is coordinated with the user's motion and use of the senses such as sight, sound, and touch. Virtual reality systems are often used to create simulations so that a user may learn or train while being exposed to little or no physical risk.

SUMMARY

Recognized herein is the need for improved methods and systems for treating a mental or neurodevelopmental disorder, such as autism. Such methods and systems can employ the use of virtual or augmented reality systems.

The present disclosure provides methods and systems for treating or supplementing the treatment of a subject for a mental or neurodevelopmental disorder, such as autism, using a virtual or augmented reality system. The method can comprise placing the subject in a virtual world using a virtual or augmented reality system that provides visual, auditory, and/or haptic stimulation, monitoring the subject's interaction with the virtual and real world, and measuring the subject's progress toward one or more therapeutic goals. The virtual or augmented reality system can comprise a display screen for visual engagement, headphones or speakers for auditory stimulation, and controllers for physical input as well as haptic feedback. Monitoring may be in real-time The method may further comprise the subject interacting with the virtual world using eye movement, head movement, and/or one or more controllers attached to a body and/or limb of the subject. One or more sensors integrated or external to the virtual or augmented reality system may detect the subject's interactions with the virtual world.

The method may further comprise the subject interacting with a therapist, parent, or peer to progress toward the one or more therapeutic goals. For example, the subject may be paired with the therapist, parent, or peer, or a plurality of therapists, parents, or peers, or any combination of the above. In some instances, a paired individual or entity may be capable of influencing the subject's experience in the virtual world, such as by creating, modifying, and/or removing the visual, auditory, and/or haptic stimulations provided to the subject in the virtual world.

In some instances, the virtual or augmented reality experiences and therapies can be tailored to the needs of individual subjects either manually by a human expert (e.g., therapist) or using computer algorithms or artificial intelligence. For example, the tailoring can be performed based at least on prior conditions of the subject and/or based on data collected throughout the subject's and others' use of the system.

In some instances, different virtual or augmented reality experience may be organized in a library and be available for prescription or recommendation by the human expert or computer algorithms (e.g., artificial agent) to care givers, parents, or the subjects themselves.

In an aspect, provided is a method for treating or supplementing treatment of a subject with mental or developmental conditions, comprising: (a) placing the subject in a virtual world using a virtual or augmented reality device that provides visual, auditory, or haptic stimulation; (b) presenting the subject's virtual or augmented reality experience on a display external to the virtual or augmented reality device; (c) generating, via one or more sensors operatively coupled to the virtual or augmented reality device, sensory data of the subject in response to the visual, auditory, or haptic stimulation, wherein the sensory data is indicative of the subject's progress toward one or more therapeutic goals; and (d) evaluating at least the subject's virtual or augmented reality experience presented on the display and the sensory data to determine the subject's progress toward one or more therapeutic goals.

In some embodiments, the subject is capable of interacting with the virtual world using eye movement, head movement, or one or more controllers attached to a body and/or limb of the subject.

In some embodiments, the subject is capable of interacting with a therapist, parent, or peer to progress toward the one or more therapeutic goals.

In some embodiments, the method can further comprise prescribing the one or more therapeutic goals to the subject.

In some embodiments, the therapist, parent, or peer is located remote from the subject.

In some embodiments, the visual, auditory, or haptic stimulation is provided by the therapist, parent or peer.

In some embodiments, the method is performed without direct supervision of the subject.

In another aspect, provided is a method for treating a subject for autism, wherein the subject is or is suspected of being autistic, comprising: (a) presenting one or more images or video to the subject using a virtual or augmented reality system, wherein the virtual or augmented reality system comprises a first display screen for presenting the one or more images or video to the subject; (b) generating, via one or more sensors operatively coupled to the virtual or augmented reality device, sensory data of the subject in response to the one or more images or video, wherein the sensory data is indicative of the subject's progress toward one or more therapeutic goals; and (c) evaluating at least the sensory data to determine the subject's progress toward one or more therapeutic goals.

In some embodiments, the subject is further presented with audio using the virtual or augmented reality system.

In some embodiments, the one or more sensors comprise at least one of a group consisting of cameras, microphones, motion sensors, heat sensors, inertial sensors, and touch sensors.

In some embodiments, the subject is capable of interacting with the one or more images or video using eye movement, head movement, or one or more controllers attached to a body and/or limb of the subject.

In some embodiments, the subject is capable of interacting with a therapist, parent, or peer to progress toward the one or more therapeutic goals.

In some embodiments, the therapist, parent, or peer is located remote from the subject.

In some embodiments, the one or more images or video is presented by the therapist, parent or peer.

In some embodiments, the evaluating comprises comparing the sensory data to expected data for the one or more therapeutic goals.

In another aspect, provided is a method for diagnosing a user with mental or developmental conditions, comprising: (a) placing a plurality of subjects having a first mental or developmental condition in a virtual world using one or more virtual or augmented reality devices, wherein the virtual world provides one or more of visual, auditory, and haptic stimulation; (b) generating, via a first set of one or more sensors operatively coupled to the one or more virtual or augmented reality devices, a first set of sensory data of the plurality of subjects in response to the one or more of visual, auditory, and haptic stimulation, wherein the first set of sensory data is indicative of the first mental or developmental condition; (c) placing the user in the virtual world using a virtual or augmented reality device; (d) generating, via a second set of one or more sensors operatively coupled to the virtual or augmented reality device, a second set of sensory data of the user in response to the one or more of visual, auditory, and haptic stimulation; and (e) comparing the second set of sensory data to the first set of sensory data to diagnose the user with the first mental or developmental condition.

In some embodiments, the plurality of subjects is capable of interacting with a therapist, parent, or peer in the virtual world.

In some embodiments, the therapist, parent, or peer is located remote from the plurality of subjects.

In some embodiments, the one or more of visual, auditory, and haptic stimulation is provided by the therapist, parent or peer.

In some embodiments, the method is performed without direct supervision of the user.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 6A shows a user using a user device. FIG. 6B shows the user using the user device immersed in a virtual reality or augmented reality experience. FIG. 6C shows an exemplary display of the sensory module as seen by the user.

DETAILED DESCRIPTION

Figure 1:
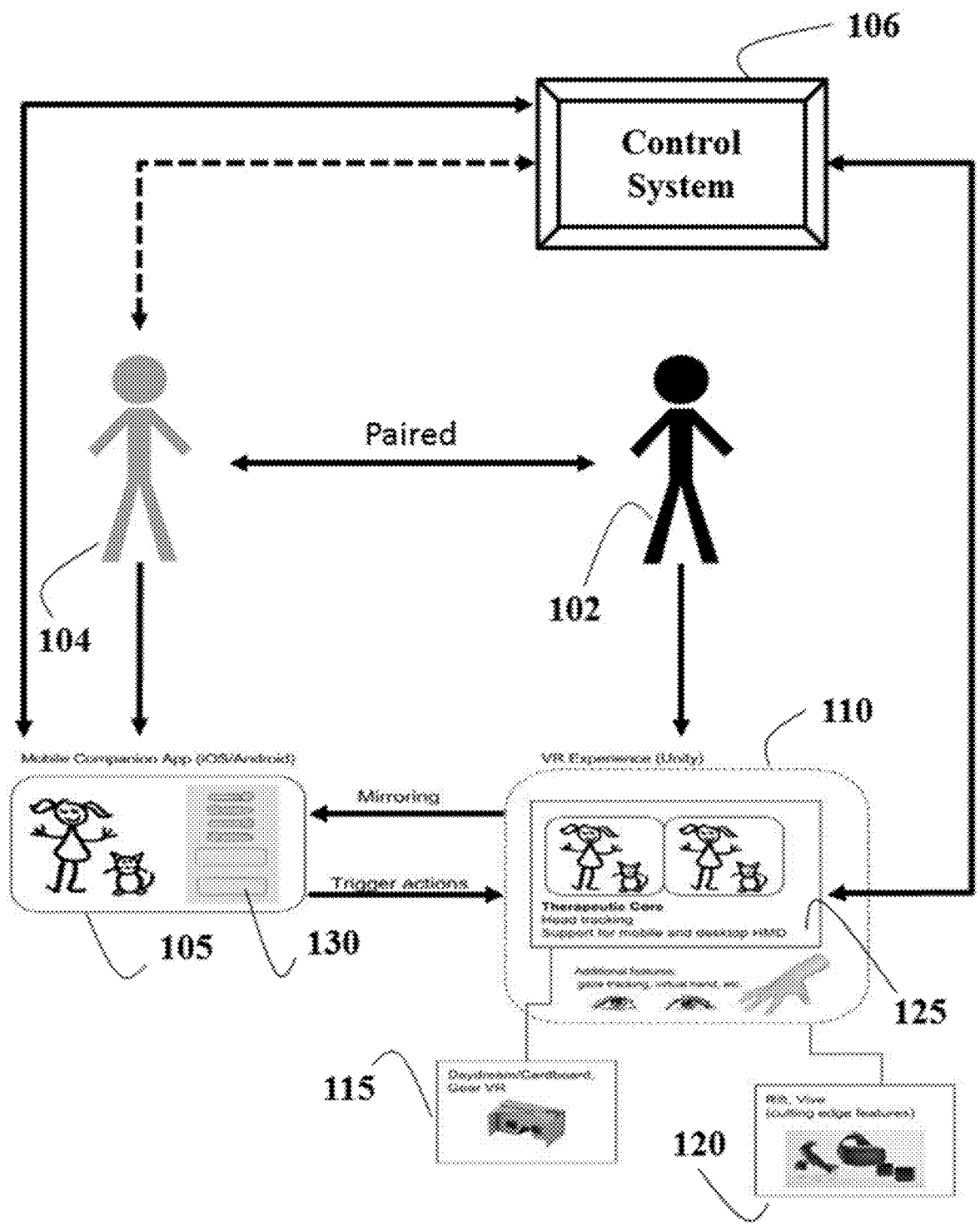
FIG. 1 shows a schematic illustration of a virtual or augmented reality system.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Virtual Reality (VR) or Augmented Reality (AR) Therapy

In an aspect, provided are systems and methods for treating a subject for a mental or developmental disorder, such as, for example, autism, attention deficit hyperactivity disorder (ADHD), and social anxiety disorder. This may comprise using a virtual or augmented reality system to place the subject in a virtual world, where the subject can be presented with visual, auditory, and/or haptic stimulation, monitoring the subject's interaction with the virtual and/or real world, and measuring the subject's progress toward one or more therapeutic goals. The subject's interactions, reactions, and/or responses to the stimulations presented in the virtual world can be quantified based at least in part on sensory data measured for the subject, such as a reaction time, gaze accuracy, gaze stability, response volume, and/or other forms or units of outputs by the subject. In some cases, the subject's progress toward one or more therapeutic goals can be quantified based at least in part on such quantifications. The subject's progress toward one or more therapeutic goals can also be measured based on qualitative observations made by another user monitoring the subject's interactions, reactions, and responses in the virtual world, such as a therapist, operator, or supervisor. For example, the subject's progress toward one or more therapeutic goals can be measured based on subjective and/or objective feedback from the monitoring user.

The systems and methods can be used for treating the subject for a given mental or developmental disorder, such as autism. The systems and methods can be used for treating a subject suffering a deficiency in a given social skill (e.g., ability to retain attention). The virtual world, and the one or more stimulations (e.g., visual, auditory, haptic) presented in the virtual world, can be designed to treat the given mental developmental disorder and/or improve the given social skill. For example, the virtual world can be tailored for a given mental or developmental disorder. Alternatively or in addition, the virtual world can be tailored for a given social skill. Alternatively or in addition, the virtual world can be tailored for a subject. One or more parameters and/or stimulations in a virtual world can be provided or adjusted in real-time, such as by another user (e.g., therapist, operator, supervisor) monitoring the subject in the virtual world, for example, based on the subject's interactions, reactions, or responses (or lack thereof) to a previous stimulation.

Visual stimulation may be provided by presenting one or more images or video on a display screen. Auditory stimulation may be presented through one or more headphones or speakers of the virtual or augmented reality system. The one or more headphones or speakers may be synchronized with images or video provided by the display screen to the subject. Haptic stimulation may be presented through one or more controllers attached (or otherwise coupled) to the body and/or limb of the subject. The monitoring may permit another individual, such as a supervisor, to monitor treatment. The supervisor may be a therapist, an operator, a teacher, or a parent. The monitoring may or may not be remote. The monitoring may be over one or more networks.

The subject may interact with the virtual world using eye movement, head movement, or one or more controllers attached to the body and/or the limb of the subject. To track the subject's movement, the system may employ one or more sensors, including one or more cameras. The system may employ other optical sensors, auditory sensors (e.g., microphones), touchpads, touchscreens, motion sensors, heat sensors, inertial sensors, touch sensors, or other sensors. The one or more sensors may be capable of measuring sensory data indicative of an output by a subject (e.g., eye movement, head movement, facial expressions, speech, etc.).

The subject may interact with a therapist, supervisor (e.g., parent), or peer to progress toward the one or more therapeutic goals. The therapist, supervisor, or peer can be located remotely from the subject.

The systems and methods may allow a therapist to prescribe one or more therapy sessions to achieve one or more therapeutic goals to a subject. The subject may perform the prescribed therapy sessions, without direct supervision from the therapist prescribing the therapy sessions. In some instances, the therapy sessions are capable of being reviewed at a later time and place. Alternatively or in addition, the therapy sessions are capable of being monitored directly or indirectly (e.g., remotely) in real time. In some instances, the therapy sessions can be monitored by another individual, such as a parent or guardian in real time or at a later time and place.

A method for treating a mental or developmental disorder may comprise using a virtual or augmented reality system to present one or more images or video to the subject. The virtual or augmented reality system can comprise a display screen for presenting the one or more images or video to the subject. The method may comprise monitoring, in real time, a response of the subject to the one or more images or video presented to the subject in the virtual or augmented reality system. As used herein, real time can include a response time of less than 1 second, tenths of a second, hundredths of a second, or a millisecond. Real time can include a process or operation (e.g., monitoring of an action by a subject) occurring simultaneously or substantially simultaneously with another processor or operation (e.g., performing the action by the subject).

The method may further comprise presenting audio to the subject in the virtual or augmented reality system. The audio may be presented through one or more headphones or speakers of the virtual or augmented reality system. The one or more headphones or speakers may be synchronized with images or video provided by the display screen to the subject. The method may comprise monitoring, in real time, a response of the subject to the audio presented to the subject in the virtual or augmented reality system.

The method may further comprise presenting haptic output to the subject in the virtual or augmented reality system. The haptic output may be presented through one or more controllers of the virtual or augmented reality system. The one or more controller may be synchronized with images or video provided by the display screen to the subject and/or the audio provided by the one or more headphones or speakers to the subject.

The method may further comprise monitoring the subject with the use of one or more sensors, including one or more cameras. A camera may be a charge coupled device (CCD) camera. The camera may record a still image or video. The image or video may be a two-dimensional image or video or a three-dimensional image or video. The system may employ other optical sensors, auditory sensors (e.g., microphones), touchpads, touchscreens, motion sensors, heat sensors, inertial sensors, touch sensors, or other sensors. The one or more sensors may be capable of measuring sensory data indicative of a subject's progress toward one or more therapeutic goals, such as a reaction time, gaze stability, gaze accuracy, response volume, the presence or lack of a movement, the presence or lack of speaking, or other outputs by the subject.

The virtual or augmented reality system may be a virtual reality system in which the subject is presented with content in an environment that may be separate from the surrounding of the subject. Alternatively, the virtual or augmented reality system may be an augmented reality system in which the subject is presented with content that may be overlaid or at least partially integrated with the environment of the subject.

Such system can comprise a display for presenting the subject with content. Such display can be provided to the subject through a user device (e.g., mobile device, computer, tablet, laptop, etc.), for instance. The user device may or may not be portable. Such system can further comprise one or more headphones, earphones, or speakers for presenting the subject with audio. The one or more headphones, earphones, or speakers may be synchronized with images or video provided by the display screen to the subject. The subject may access the virtual or augmented reality system with the use of a supplemental headgear (e.g., Google® Daydream/Cardboard, Oculus® Gear/Rift, and HTC® Vive). Such system can further comprise one or more controllers for presenting the subject with haptic output. The controllers can be configured to, for example, vibrate. The controllers can comprise an actuator. The controllers may be attached (or otherwise coupled) to one or more body parts of the subject. The display can receive the one or more images or video, the headphone, earphone, or speaker can receive the audio, and the controllers can receive the haptic output to present to the subject through a computer control system.

Using the virtual or augmented reality systems may advantageously provide various therapeutic values to a subject (or user) receiving treatment. The subject having or suspected of having a neurodevelopmental disorder, such as autism, may be treated by receiving VR or AR content through the system.

Subjects who can benefit from these methods can be divided into characteristic groups. One group may comprise individuals with cognitive or perceptual conditions that need a more gentle and controlled introduction to certain aspects of the real world. These cognitive or perceptual conditions may include mental conditions such as a variety of phobias (e.g., arachnophobia, agoraphobia, acrophobia, social phobia and anxiety disorder), disorders involving distortions in the perception of one's own body (e.g., anorexia nervosa), and any mental or neurological condition that can cause sensory overload (e.g., ADHD). One group may comprise individuals who have conditions that prevent them from acquiring, or make it difficult for them to acquire, skills (e.g., social skills) through the normal course of development or the natural course of recovery from a trauma or disease. This may include individuals with autism, individuals with social (pragmatic) communication disorder, as well as those individuals that require language therapy, occupational therapy, behavioral therapy or physical therapy. One group may comprise a diverse group of individuals that can benefit from novel intervention methods that were not possible outside of virtual reality (VR) or augmented reality (AR). This group may include individuals diagnosed with conditions that can improve by having the individual observe and involve oneself in conversation in a virtual world to improve self-compassion or self-esteem (the lack of which are both symptoms of clinical depression). The group may also include any and all individuals in the general population that may benefit from practicing social skills or routines in a controlled environment.

Furthermore, beneficially, the VR or AR system may facilitate data collection during or subsequent to treatment. For example, a subject's progress toward one or more therapeutic goals may be measured with significantly higher accuracy and precision than traditional methods of therapy. The VR or AR system may be capable of collecting data on certain aspects of the treatment that was previously unavailable for measurements via traditional methods. For example, the VR or AR system may comprise one or more integrated sensors that are capable of measuring sensory data indicative of an output by a subject (e.g., eye movement, head movement, facial expressions, speech, etc.). The one or more sensors may be capable of measuring sensory data indicative of a subject's progress toward one or more therapeutic goals, such as a reaction time, gaze stability, gaze accuracy, response volume, the presence or lack of a movement, the presence or lack of speaking, or other outputs by the subject. For example, a user device presenting the subject with the VR or AR environment may have integrated in the user device optical sensors, auditory sensors (e.g., microphones), touchpads, touchscreens, motion sensors, heat sensors, inertial sensors, touch sensors, or other sensors capable of measuring an output by the subject. A subject's progress toward achieving a therapeutic goal (e.g., increasing ability to concentrate) may be quantified more accurately and precisely than traditional methods (e.g., that rely on manual observations of a subject or of a video recording of a subject). For example, the VR or AR system may track a patient's gaze with one or more integrated sensors that are much more accurate than manual observations that predict a direction of a gaze. Additionally, the integrated sensors in the VR or AR system allow the measuring of a subject's interactions, reactions, and responses to a situation without interrupting, or being exposed to, the subject who is wholly immersed in a VR or AR environment—for example, traditionally, the subject may become aware of the artificiality of a therapy session, such as via presence of another human or a camera, and change his or her behavior based on such awareness, resulting in biased or otherwise inaccurate results.

In some cases, data collected (or recorded) for one or more subjects may be aggregated to build behavior models for one or more conditions (e.g., mental or developmental disorders). Such behavior models can be leveraged as diagnostic tools for users to be evaluated through the VR or AR system. For example, a plurality of behavior models for different mental or developmental disorders can be stored in a library of behavior models, such as in one or more databases. A behavior model for a first type of developmental disorder can comprise data exhibited by one or more subjects known to suffer from the first type of developmental disorder when placed in a first VR or AR environment. When a user to be diagnosed is placed in the same first VR or AR environment, or an environment similar to the first VR or AR environment, the data collected on the user may be compared to the behavior model for the first type of developmental disorder to determine whether the user has the first type of developmental disorder or not, or a degree to which the user suffers from the first type of developmental disorder. In some instances, the data collected for the user to be diagnosed may be compared to a plurality of behavior models to determine which one or more conditions the user may suffer from (and to what degree). By way of example, the higher the % similarity between the collected data for the user and the data stored for the behavior model, the more likely it is (and with higher degree) that the user suffers from the condition of the behavior model.

The VR or AR system described herein may further provide a low cost, accessible therapeutic solution for subjects who have a mental or developmental disorder. Alternatively or in addition, the VR or AR system described herein may provide educational and/or entertainment value to subjects who have a mental or developmental disorder, and subjects who do not.

VR or AR content can be keyed to virtual behavioral intervention principles which may be adapted from multiple approaches used by other traditional methods of autism therapy. In some cases, naturalistic behavioral intervention techniques may be employed. Naturalistic therapy, or natural environment teaching ("NET"), may occur in the subject's natural environment. Methods and systems herein can integrate some key attributes of NET interventions into VR or AR therapy. In some examples, the system may provide the user with the opportunity to select a type of virtual reality or augmented reality content or a treatment program (e.g., selecting the type of virtual environment such as the 'zoo' or a 'train station') and encourage supervisors or other third parties monitoring the user ("supervisors") to follow established training manuals, such as the Hanen OWL guidelines which teach the Observe, Wait, and Listen technique. Under these guidelines, supervisors may let the user explore the virtual environment while observing carefully what interests the user, wait for the user to make spontaneous comments or actions, listen carefully to what the user says or signs, and plan the next steps of therapy based on these comments or signs. In some examples, the system may permit a user to create a communication or play opportunity, if needed. That is, if the user does not communicate or do anything, the system can use playful obstructions or a similar technique to create a communication or play opportunity. For instance, a user that stares at only one animal silently may begin to speak if the therapist avatar blocks the user's view of the animal, or, alternatively, the user may start a game of trying to get past the therapist. Once the user starts doing something, the therapy can return to the OWL guidelines. In some examples, the system can provide the user with prompts of varying supportiveness to complete a task if there is a specific task to complete. In some examples, the system can reward the user for succeeding in such tasks. Such reward may be, for example, an image, audio or video that is pleasing to the user, a pleasing stimulus, or a compliment from a third party (e.g., supervisor).

In doing so, the system may provide prompts of varying supportiveness throughout the process. For example, the prompts may include, in the order of least supportive to most supportive: lightweight prompts by the software (e.g., a clickable item that blinks or is slightly translucent or a virtual hand suggesting where a user can move certain blocks); leading comment by a supervisor or therapist (e.g., using suggestive phrases such as "I see something interesting" or "That animal looks hungry"); verbal instruction (e.g., telling the user directly what to do); imitative model (e.g., a therapist or supervisor in real life, or alternatively as an avatar in the virtual environment, demonstrating a desired action so that the user can imitate); and physical prompts (e.g., directing the user by using hand-over-hand support through a desired action, or moving the user's head in an intended direction). Incorporating such virtual NET-style intervention, the system can create and provide VR or AR environments with varying levels of difficulty, in which the user always succeeds in a given task, with or without supportive prompts. Through adaptations of such key principles, the system may provide goal-oriented therapies, such as, for example, therapies which build social connections, therapies which teach stories, and sensory-based therapies.

In some aspects, the system may provide therapies which may build social connections between the user and other individuals. The other individuals may include one or more subjects that are also under treatment. These therapies can include the training of developmental skills such as joint attention (e.g., eye contact), social reciprocity (e.g., taking turns), and pragmatic intentions (e.g., problem solving or communicating acceptance). For example, a therapy module for developing inferencing may help prepare the user to become capable of learning how to recognize and interpret facial expressions, and a therapy module for developing joint attention may help prepare the user to become capable of understanding other people's perspectives. In some aspects, the system may provide therapies which teach functional skills using stories. These therapies can include building a practice environment for both routine tasks such as crossing a street and non-routine tasks such as responding to fire alarms or participating in a Halloween trick-or-treating activity. Other practice environments include interacting with a police officer that a user meets in an urban street. Beneficially, such stories provide an effective and entertaining ('fun') solution to teach subjects how to navigate everyday interactions by placing the subjects in a controlled virtual or augmented reality environment, thereby shielding the subjects from potential actual harms and retaining control to effectively guide the subjects at a flexible pace.

In some aspects, the system may provide sensory-based therapies. Sensory-based therapies can include using a VR or AR environment to build specific calming or stimulating experiences with a focus on helping users with neurodevelopmental disorders or disabilities, such as autism, to manage or respond to otherwise challenging environments and situations. For example, a calming module may allow a user to play a simple and delightful musical instrument using just the direction of his or her gaze.

Monitoring a User's Virtual Reality Experience

Through virtual reality or augmented reality, the system can provide therapy through a network or graph of interactions that are triggered either by one or more actions of the user or by a supervisor or other third party that is monitoring the user. In some instances, an interaction, reaction, or response may be triggered by a peer (e.g., another subject user). Every discrete action from the user can trigger a combination of animation, audio, and/or visual instructions to the supervisor. A supervisor, who may or may not be a therapist, can directly monitor and supervise the user receiving the VR or AR therapy through the use of a companion application. Such monitoring may occur remotely, wherein the subject user and the therapist are physically and geographically at a significant distance from each other (e.g., different buildings, different countries, etc.). Alternatively or in addition, such monitoring may occur as in-room monitoring.

The system can comprise at least one or at least two devices: one device capable of providing a virtual reality or augmented reality environment (e.g., smartphone, dedicated headset device like an HTC® Vive, Google® Cardboard headset) to the user, and the same device, or a second device, capable of providing a companion application to the supervisor. The at least two devices can be communicatively coupled together, such as via tangible connection cable or wireless or Bluetooth pairing. Through the companion application, a supervisor may access, and, if needed, intervene in, the user's virtual or augmented reality experience. As an alternative, the system can comprise a single integrated device.

FIG. 1 shows a schematic illustration of a virtual or augmented reality system. A user 102 may be paired with a supervisor 104. The user 102 may be a subject. The user 102 may have a condition, such as a mental or developmental disorder (e.g., autism). The user 102 may access a virtual reality or augmented reality experience 110 via a first user device. The first user device may be any device comprising one or more displays, such as a monitor, screen, mobile phone, computer, smartphone, laptop, tablet, television, smart television, or other device. For example, the user 102 may access the experience 110 through the use of supplemental headsets 115 and 120 (e.g., Google® Daydream/Cardboard, Oculus® Gear/Rift, HTC® Vive, etc.).

The first user device may be communicatively coupled to one or more sensors, such as described elsewhere herein. The one or more sensors may be integrated in the first user device or external to, and operatively coupled to, the first user device, such as via wired or wireless (e.g., Bluetooth, Wi-Fi, Near Field Communication (NFC), etc.) connections. The one or more sensors may be capable of collecting data on the user 102, such as the user's interactions, reactions, and/or responses to one or more components and/or stimulations in the VR or AR experience 110.

The VR or AR experience 110 may comprise one or more VR or AR scenes 125. For example, the VR or AR experience 110 may comprise a time-dependent progression of one or more VR or AR scenes 125. The VR or AR scenes 125 may be dynamic, such as comprising one or more dynamic components (e.g., animation, audio, etc.) and/or components that can be triggered to change. The user 102 may be capable of interacting with, or reacting to or responding to, one or more components of the VR or AR scenes 125. The user 102 may have a stereoscopical view of the one or more VR or AR scenes 125 in the VR or AR experience 110. The VR or AR experience 110 can be a 360° experience. The VR or AR experience 110 may be capable of presenting one or more stimulations, such as visual stimulations, audio stimulations, and/or haptic stimulations, such as via the first user device. Alternatively or in addition, the one or more stimulations may be provided via one or more external devices operatively coupled to the first user device, such as via wired or wireless connections. Such other devices can include, for example, other displays, screens, speakers, headphones, earphones, controllers, actuators, lamps, or other devices capable of providing visual, audio, and/or haptic output to the user 102.

The supervisor 104 may have access to a real-time streamed or mirrored view of the VR or AR experience 110 via a second user device. The second user device may be configured to execute a mobile companion application 105 that is programmed to display the real-time streamed or mirrored view of the VR or AR experience 110. The mobile companion application 105 may comprise software programmed to execute the present disclosure. The second user device may be any device comprising one or more displays, such as described above. In some instances, the second user device may be any device comprising a user interactive device (e.g., buttons, touchscreen, keyboard, etc.) that allows the supervisor 104 to provide an input to the second user device. In some cases, the second user device may provide the supervisor 104 with a non-stereoscopical view of the user's 102 experience 110. For example, the mobile companion application 105 may display the experience 110 in a wider field of view than is provided to the user 102 so that the supervisor 104 can see what is to the right and left of the user's view. As an alternative, the supervisor 104 may be provided with an extended view to that of the user 102 in all angles including in the diagonal, up, and down directions. As an alternative, the mobile companion application 105 of the supervisor 104 may provide such content asynchronously, such as at a later time. The mobile companion application 105 may further provide a console 130 which allows the supervisor 104 to intervene (e.g., trigger actions or prompts) in the user's 102 virtual reality or augmented reality scene 125. Such interventions may include manipulating characters in the scene, triggering audio, visual, and/or haptic change in the VR or AR environment, or taking administrative action such as starting a new learning module or ending the therapy session.

A control system 106 may provide content for the user's 102 virtual reality experience 110. In some instances, the content may be updated, modified, created, and/or removed, such as by the supervisor 104 and/or another individual or entity. The control system 106 may be hardware and/or software. In some instances, the control system 106 can reside on the first user device, such as as an application or a program. In some instances, the control system 106 can reside on the second user device, such as as an application or a program. In some instances, the control system 106 may reside on a server and/or communicate via one or more computer networks with the first user device and/or the second user device. In some instances, the control system 106 may be distributed across one or more devices (e.g., server hardware, first user device, second user device, etc.) which individually, or collectively, perform the operations of the control system 106. The control system 106 can be a computer control system, as described further below. In some cases, the control system 106 may pair the mobile companion application of the supervisor 104 with the VR or AR experience 110 of the user 102. For example, the mirroring of the VR or AR experience 110, and/or the one or more commands from the console 130 to the VR or AR experience 110 may be communicated between the first user device and the second user device through the control system 106.

Data collected about the user 102 with relation to the VR or experience 110, such as from one or more sensors, may be stored and/or transmitted to the first user device, the second user device, and/or the control system 106.

Figure 2:
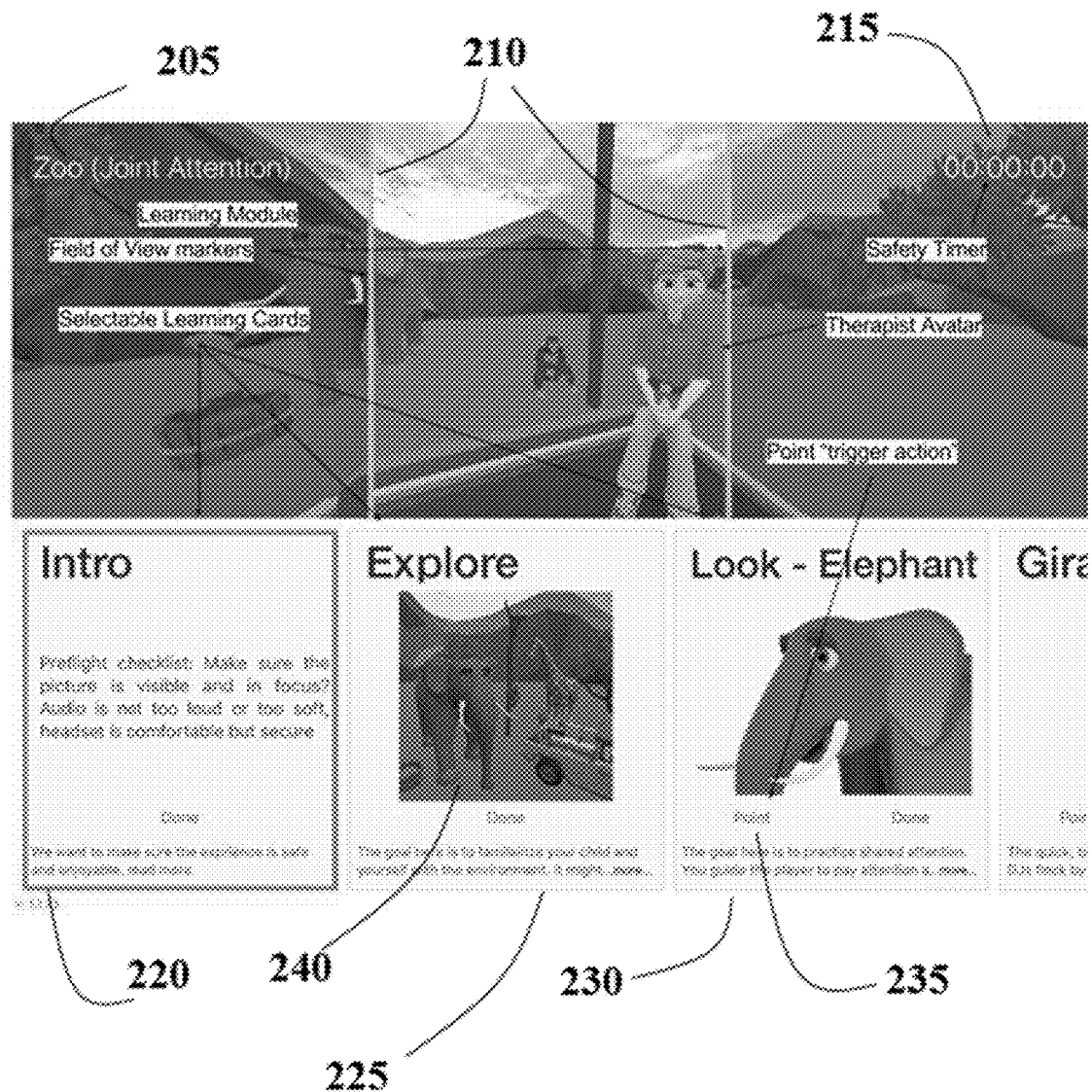
FIG. 2 shows an illustration of a mobile companion application display.

FIG. 2 shows an illustration of what a mobile companion application may display to a supervisor of a user. The mobile companion application 200 may comprise "field of view" markers 210 distinguishing the boundary between what the user is viewing and the extended view of the supervisor. These "field of view" markers 210 need not be limited to the left and right boundaries, and, in the alternative, can mark the boundaries in other directions, including the diagonal, up, or down directions. The supervisor may further be provided with a selection of learning cards 220, 225, 230 (e.g., "Intro," "Explore," "Look—Elephant," "Giraffe"), including actions 235 to trigger (e.g., "Point") and thumbnail pictures 240 of the selection of learning cards 220, 225, and 230. The companion application display may also include an indication of the learning module 205 that the user is "playing" and a display of progress checking mechanisms 215 such as a safety timer.

In one embodiment, more devices may be paired, as needed, for increased monitoring. For example, a second companion application that provides a camera view can be used as an in-room monitor. A therapist may view the user in a VR or AR session through a small video window on the companion application interface. For example, a user device of a user may be paired with at least about 2, 3, 4, 5, 6, 7, 8, 9, 10, 15, 20, 25, 30, 35, 40, 45, 50 or more devices of supervisors, each having their own device. Alternatively or in addition, a user device of a user may be paired with at most about 50, 45, 40, 35, 30, 25, 20, 15, 10, 9, 8, 7, 6, 5, 4, 3, or 2 devices of supervisors. In some cases, a supervisor may be paired with a plurality of users. For example, a user device of a supervisor may be paired with at least 2, 3, 4, 5, 6, 7, 8, 9, 10, 15, 20, 25, 30, 35, 40, 45, 50 or more devices of users, each having their own device. Alternatively or in addition, a user device of a supervisor may be paired with at most about 50, 45, 40, 35, 30, 25, 20, 15, 10, 9, 8, 7, 6, 5, 4, 3, or 2 devices of users. In some cases, a virtual reality experience may allow a plurality of users (e.g., peer subjects) to interact with each other in the virtual reality experience, such as for a group therapy session.

In one embodiment, the pairing of these devices (e.g., devices for supervisors, devices for users, etc.) may be remote which allows for teletherapy sessions. The devices can be paired over a network, such as over the internet, intranet, and/or extranet, so that the companion application may operate remotely from the user.

Figure 7:
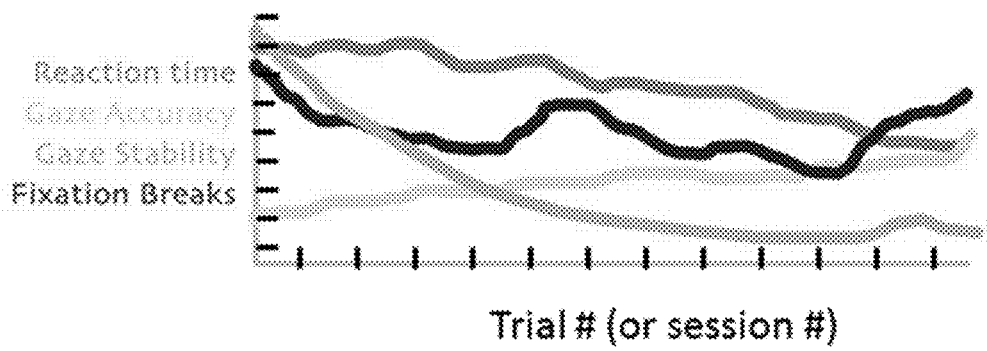
FIG. 7 shows an illustration of a progress report generated from a user's response to an augmented reality or virtual reality experience.

In one embodiment, the system can use a gaze tracking algorithm to determine the object of focus for the user and trigger actions and prompts based on that gaze. The system may use such tracking algorithm to collect metrics and provide an analytics dashboard comprising data such as reaction time to a task, whether the user is taking fixation brakes, gaze accuracy, and how steady their gaze is on an object versus a neurotypical user. Alternatively, the system may compare the user with other subjects receiving the same or similar treatments. These analytics may provide not only the metrics tracked during the user's session but also a longitudinal view of the user's performance progress. See FIG. 7 for an illustration of an analytics dashboard. This dashboard may be used as a user progress report and contain information such as task category, task name, start date, total number of sessions, total number of minutes, total number of trials, total number of successes, success rate, best week, user profile data including such things as, for example, user age and gender, and a graphical illustration of the progress of the user such as, for example, user's reaction time, gaze accuracy, gaze stability, and fixation breaks. The dashboard may contain supplemental analytics on each progress category based on the goals of the training objective (e.g., Total Minutes: "Exceeds 10 minutes per session effective session duration"; Total Trials: "Meets minimum effective repetitions per session"; Success Rate: "Exceeds expected 75% success rate", Total Sessions: "18 left out of 150 Recommended Total"). The dashboard may contain other sensory data, such as measured by the one or more sensors described elsewhere herein. The sensory data can be indicative of a subject's progress toward one or more therapeutic goals, such as a reaction time, gaze stability, gaze accuracy, response volume, the presence or lack of a movement, the presence or lack of speaking, or other outputs by the subject. The sensory data can comprise data otherwise undetectable or difficult to detect or quantify with traditional therapy methods.

In one embodiment, the system can integrate motion controllers into the therapy modules to track the user's motions in the virtual or augmented reality system. For instance, in a joint attention module where the user is evaluated on his or her ability to respond to pointing, there may be a lesson where the user can point in real space holding a controller. The system can then track where the gesture lands in the virtual or augmented reality space and base actions and prompts accordingly. In another instance, in a module where the user is trained for interaction with the police, the same motion tracking capability may track the hand position of the user to determine if the user is exhibiting behavior that may put them in danger with the police.

In one embodiment, the system can integrate voice recognition technology to enable therapeutic conversation training for the user in the VR or AR space. For instance, a user may be given simple scenarios where the user answers the door and finds themselves having a back and forth conversation with a virtual character that leverages voice recognition mixed with override input from the supervisor to create a coherent training environment.

Virtual Reality Content

Translating therapeutic goals and abstract processes into concrete virtual reality or augmented reality may be a multidisciplinary endeavor which can involve the coordination and communication of experts in as many fields as psychology, medicine, speech-language therapy, occupational therapy, physical therapy, behavioral intervention, game design, software development, and visual and auditory arts. The system can facilitate such multidisciplinary coordination by systematically categorizing the therapeutic content into distinct units, such as "learning modules" and "learning cards." A learning module can represent a developmental milestone objective for the user. It can comprise a distinct set of therapeutic content that attempts to improve one or more target skills in the user. In some aspects, the system may comprise a collection of learning modules from which a supervisor may select to opt into to "play" with a user.

Figure 3:
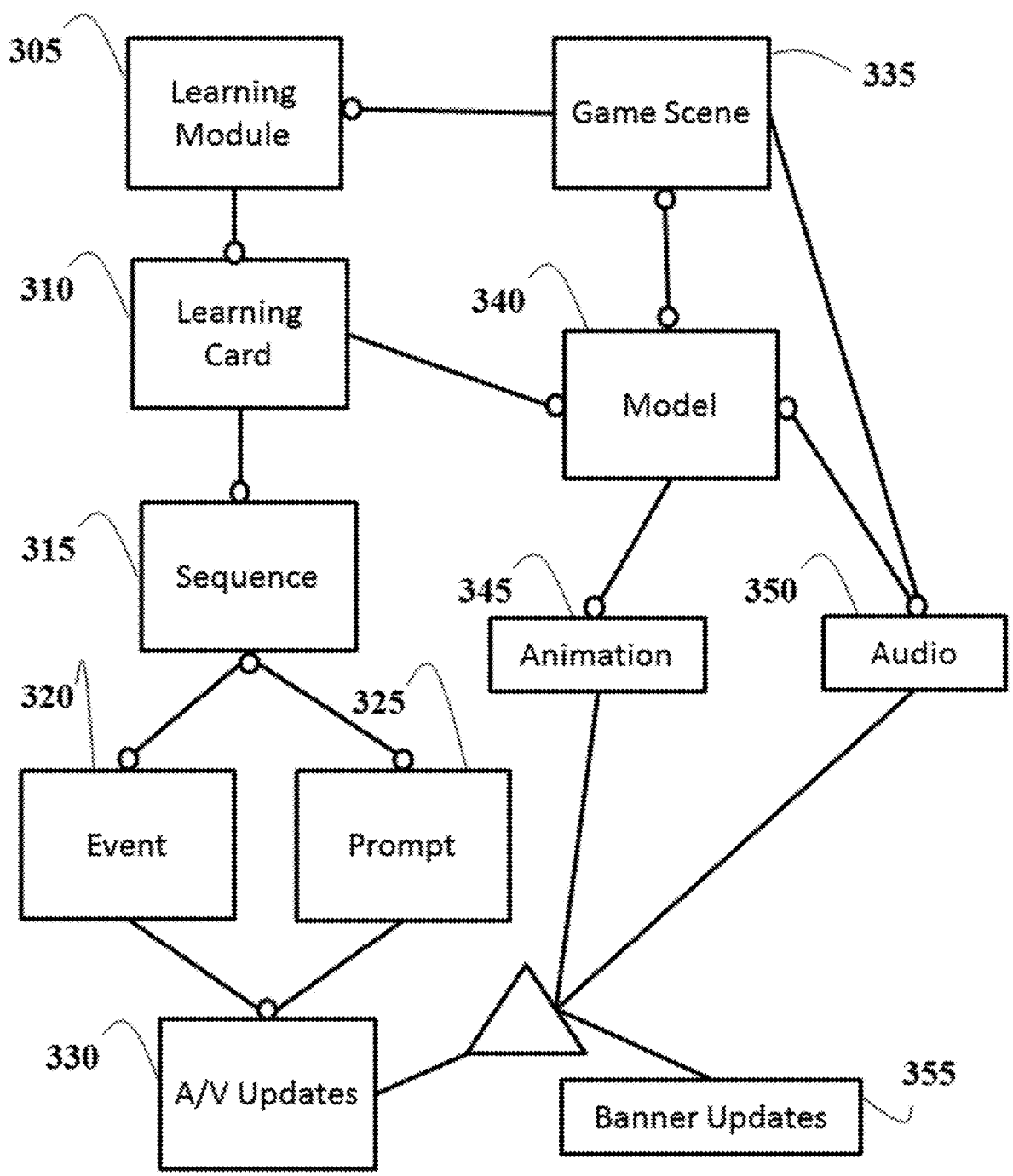
FIG. 3 shows a logical model of a learning module.

FIG. 3 depicts a logical model for a learning module 305. In FIG. 3, each line ending with a circle denotes a "one to many" relationship, in which a line connector represents "one" and a circle connector represents "many." For example, a line ending with circles on both ends will denote a "one to many" relationship in both directions. Each triangle denotes an "is a" relationship.

In this logical model, each game scene 335 may comprise one or more learning modules 305, one or more models 340 (e.g., avatar, 2-D or 3-D animated characters), and one or more audio 350. Each learning module 305 may then comprise one or more learning cards 310. Each learning card 310 may comprise one or more models 340 and one or more sequences 315. Sequences 315, which can be triggered by user events 320 or application prompts 325, can comprise one or more events 320 as well as one or more prompts 325. Each of the events 320 and the prompts 325 may in turn comprise one or more sequences 315. That is, for example, a sequence 315 may trigger an event 320, and the event 320 may also trigger a sequence 315. Additionally, each of the event 320 and the prompt 325 may comprise one or more audio/visual updates 330 ("A/V updates"). Each A/V update 330 may comprise a banner update 355 in the supervisor's application as well as an animation 345 and audio 350 element in the game scene 335. One model 340 (e.g., an animal character) may relate to one or more game scenes 335 (e.g., zoo, train station), and comprise one or more animation 345 elements and one or more audio 350 elements. An audio 350 element may comprise one or more models 340.

As discussed briefly above, a learning module 305 can represent a developmental milestone in the form of a distinct set of therapeutic content that attempts to improve one or more target skills in the user. A supervisor may opt into a learning module 305 to "play" with a user. Each learning module 305 may be defined by the following parameters: title (e.g., "Safari"), educational focus (e.g., joint attention), unity scene (e.g., "Safari"), thumbnail image, and a collection of learning cards 310, including an Intro Learning Card. A unity scene, or the game scene 335, may comprise the game board, including the scene background and audio 350 elements independent of the models 340 (e.g., introductory music, generic background sounds), and a collection of two or three dimensional models 340, which normally includes the supervisor's avatar.

A learning card 310 can be a distinct playable unit within a learning module 305 that has a set of learning objectives. That is, a learning card 310 may represent a single exercise that helps move the user toward the milestone encompassed by the learning module 305. A learning card 310 may define which of a game scene's 335 models 340 are present and include a collection of sequences 315. These sequences 315 may interact both with a supervisor's companion application, such as through banner updates 355, and with the game scene 335 and models 340, such as through the animation 345 and audio 350 elements. Each learning card 310 may be defined by the following parameters: title, thumbnail image, a collection of sequences 315, and educational description, which is a long-form content that describes the purposes of the particular learning card 310. The logical flow of a learning card 310 is discussed in further detail with the discussion of FIG. 4.

A sequence 315 may be a collection of prompts 325 and events 320 that together progresses the user through some or all of the objectives of the learning card 310. A sequence 315 may be triggered either by an event 320 (e.g., the user fixes their gaze on an animal) or by an action prompt 325 on the learning card 310 which is initiated by a supervisor (e.g., the supervisor presses a button to "Point" at a Giraffe model 340). A sequence 315 may be defined by the following parameters: the event 320 or prompt 325 that triggers the sequence 315 and the collection of events 320 and prompts 325 within the sequence 315.

An event 320 may be a user action that may be explicitly captured by the VR or AR system for the purposes of triggering A/V updates 330 and/or updating active sequences 315 that contain the event 320. An event 320 may be defined by the following parameters: the user's triggering action (e.g., maintaining gaze on the Pig model 340 for 2 seconds), and a defined set of A/V updates 330 that execute as a post-action to the triggering action (e.g., a banner 355 status update in the supervisor's companion application reading, "User has gazed at Pig," or the Pig model 340 initiating an audio 350 element such as "Oink" in the game scene 335).

A prompt 325 may be a supervisor-initiated component of a sequence 315. It may be defined by the following parameters: a named action which appears as a button for the learning card 310 (e.g., a "Point" button), clear logic for a user to complete the prompt 325, a collection of A/V updates 330 should the user fail to follow the given prompt 325 which may include a banner 355 status update to the supervisor (e.g., "Tell the user to look at the Pig if they are not picking up the visual pointing cue" displayed to the supervisor in a companion application) or an animation 345 or audio 350 update in the game scene 335 (e.g., Pig model 340 is animated 345 and/or makes a sound 350), a collection of A/V updates 330 should the user succeed in following the given prompt 325 which may include a banner 355 status update to the supervisor (e.g., "Congratulate user for looking at the Pig Model" displayed to the supervisor in a companion application) or an animation 345 or audio 350 update in the game scene 335 (e.g., Pig model 340 is animated 345 or an audio 350 is initiated for celebratory music).

An A/V update 330 may be in the form of updates to the supervisor through a banner update 355, the triggering of animation 345 or audio 350 of the models 340 in the game scene 335, or the triggering of audio 350 in the game scene 335 level independent of the models 340. For example, an A/V update 330 may be defined by the following parameter: which of banner 355, animation 345, or audio 350 is to be updated (e.g., in the case of a banner update 355, the text should be specified).

Figure 4:
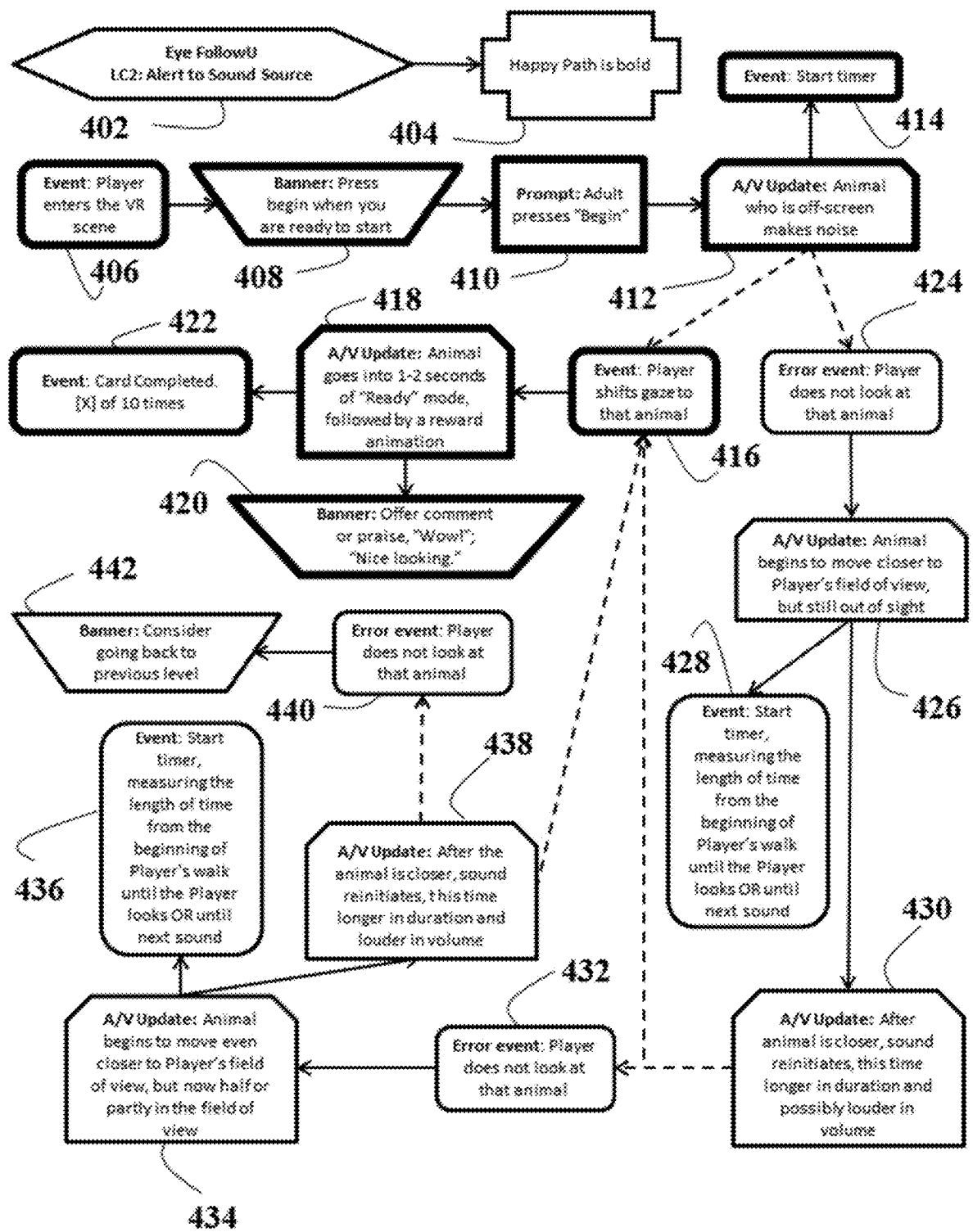
FIG. 4 shows a logical model of a learning card.

FIG. 4 shows a logical model for an illustrative learning card, element 310 in FIG. 3, titled "Eye FollowU—LC 2: Alert to Sound Source" 402. The "Eye FollowU" learning card 402 is illustrative of the logical components and methods introduced in FIG. 3 and discloses but one design of many possible. "Eye FollowU" 402 is a Card whose educational focus is joint attention. The skill within joint attention is alerting to a sound source. The player profile for the Card 402, that is, the type of affected individual for which the Card 402 is intended, is an individual who does not readily respond to the sound in his or her environment and likely has difficulty responding when his or her name is called. The behavioral goal for the Card 402 is for the user to shift his or her gaze to look at an animal model, element 340 in FIG. 3, that has produced a sound and hold the gaze on that animal for at least 2 seconds. The Card 402 may be completed when the user demonstrates this behavior at least 5 times. The Card may have the following parameters: Unity Scene (Safari); Models (Elephant, Gorilla, Adult Avatar); Thumbnail Image (figure with hand cupping ear); Sequence ([Animal] [makes appropriate animal sound]).

In an example, the Card 402 may separately provide the following notes and instructions to the supervisor in the companion application:

"This Card is for teaching the player to alert to the sound of the animal, a skill which he or she will need as he progresses through the Learning Cards. This is not intended as a 'directions following' game. So, don't tell the player to look for an animal. Let the program do the work and then join in the fun."

"LISTEN for the animal sound. WAIT for the player to find the animal. THEN, respond, offering clues only if necessary."

"Feel free to give verbal praise or comments after the Player looks at the animal."

"If the player is having trouble identifying the animal that goes with the sound, try going back to the exploratory level."

FIG. 4 illustrates the possible logical flow paths of this Learning Card 402 in action. In FIG. 4, each solid black arrow represents a definite sequence and each broken arrow represents one of many sequential options that are available.

In the logical design of the Learning Card 402, producers of the Card, such as the developers or designers, may highlight a "Happy Path" 404. The Path 404 may highlight (e.g., bold, color) the expected sequential path of a successful user, that is, a user who successfully completes the learning objective task given by the learning card. For the "Eye FollowU" Card 402, the execution sequence 406-422 is bolded as the Happy Path 404. Such highlighting may be made visible only within the system's internal design process, such as to developers or designers of the Card 402, for reference and design purposes.

The Card's 402 first event 406 occurs when the user enters the VR or AR scene. Upon the occurrence of this event 406, the supervisor receives a banner update 408 on the companion application reading, "Press 'Begin' when you are ready to start." The supervisor initiates a prompt 410 when the supervisor presses the "Begin" button on his companion application. Upon initiation of the prompt 410, there is an A/V update 412 in the VR or AR scene, and an animal model that is off-screen makes a noise. Simultaneously, the A/V update 412 starts a timer 414 to collect metrics on the user. After hearing the animal noise, the user may proceed with one of two events, the first event 416 in which the user successfully shifts his or her gaze to the noise-making animal model, and the second event 424 in which the user fails to look at the animal model. The user's success 416 in shifting his or her gaze initiates an A/V update 418 in which the supervisor receives a banner update 420 reading, "Offer comment or praise: 'Wow!'; 'Nice looking,'" and in the game scene the animal model goes into 1 to 2 seconds of "Ready" mode, followed by a reward animation 418. An example of an animal model in "Ready" mode 418 may be a three-dimensional elephant model jumping on all fours for 2 seconds. After the reward animation, the Card is marked completed "[x] of 10 times," 422 and the same message is displayed in the supervisor's companion application in a banner update. Alternatively, in other designs, the Card can be marked completed only after a user has completed the task a [y] number of times. If, on the other hand, the user fails to look at the animal model that made the noise 424, another A/V update 426 is initiated where the animal model begins to move closer to the user's field of view, but still remains out of sight. This update 426 triggers another program event 428 which starts a new timer that measures the duration of time from the beginning of the user's walk to either the time the user looks at the animal model or the time the animal model makes the next sound. After the animal model moves closer, in another A/V update 430, the sound reinitiates, this time longer in duration and possibly louder in volume. At this point, again, the user can proceed with one of two events, the first event 416 in which the user successfully shifts gaze to the noise-making animal model, and the second event 432 in which the user fails for a second time. The user's success will trigger the same sequence of A/V updates and events 416-422 as when the user succeeded on gazing at the first instance of the noise. If the user fails, another A/V update 434 is triggered, and the animal model is made to move even closer to the user's field of view, but now half or partly in the field of view of the user. After the animal model has moved partly within the view of the user, in another A/V update 438, the sound reinitiates, in longer duration and louder volume than the second instance of the noise. Another timer starts 436 measuring the duration of time from the beginning of the user's walk until either the user shifts his or her gaze on the animal model or the animal model makes the next sound. At this point, again, the user may proceed with one of two events, the first event 416 in which the user successfully shifts gaze to the noise-making animal model, and the second event 440 in which the user fails for the third time. The user's success will trigger the same sequence of A/V updates and events 416-422 as when the user succeeded on gazing at the first instance of the noise. This time, however, the user's failure will trigger a banner update 442 in the supervisor's companion application that reads "Consider going back to the previous level." From this logical model, the system can collect a number of data points including the number of times a user alerts to the sound source, which animal models the user responds to, the time it takes the user to alert to the sound source, and a ratio between the number of times the user had the opportunity to react to the sound to the number of times the user actually reacted. Such data may be presented to a supervisor as a progress report of the dashboard format illustrated in FIG. 7 or, alternatively, as any other format or report.

In other designs, the number of iterations, or attempts given to the user, for a certain learning exercise may be modified as needed and depending on the difficulty level of the particular learning card or learning module.

In some aspects, the system may provide teaching modules which teach functional skills using stories. These teaching modules can include placing a subject in a practice environment for both routine and non-routine tasks. Beneficially, such stories provide an effective and entertaining solution to teach subjects how to navigate everyday interactions by placing the subjects in a controlled virtual or augmented reality environment, thereby shielding the subjects from potential actual harms and retaining control to effectively guide the subjects at a flexible pace.

Figure 5:
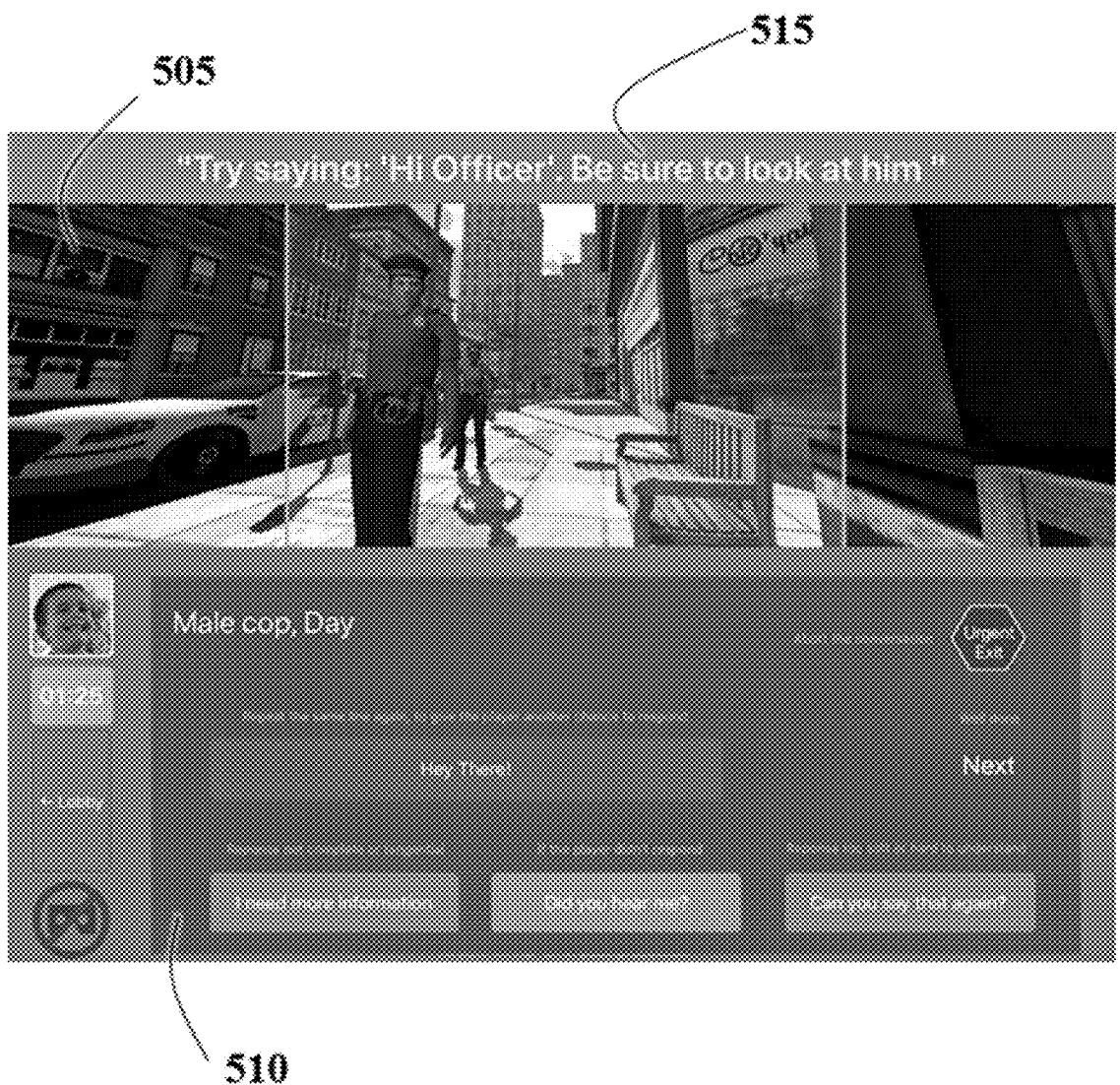
FIG. 5 shows an illustration of a teaching module display for a supervisor.

FIG. 5 shows an illustration of a teaching module display for a supervisor. The teaching module can be a learning module, as described elsewhere herein. The teaching module can comprise a practice environment for interacting with a police officer that a user meets in an urban street. For example, the teaching module can be configured to teach users conversation skills by prompting them to answer questions from a police officer avatar that approaches them on an urban street. A companion application of a supervisor may comprise an interface 500 to control the avatar. The interface 500 may include a mirrored view 505 of the user's VR or AR experience. The mirrored view 505 of the user's VR or AR experience may be a non-stereoscopical view and/or an extended view of the user's VR or AR experience. The interface 500 may comprise one or more guidelines to distinguish the user's view and the extended view. The interface 500 may comprise one or more prompts 515 displayed to the user.

The interface 500 may comprise a console 510 allowing the supervisor to trigger or prompt the user, such as by controlling the police officer avatar. For example, the supervisor may select an option to speak up when the response is not clear (e.g., control avatar to say "Can you say that again?"), select an option to require more information when the response is incomplete (e.g., control avatar to say "I need more information"), or select an option to repeat a question or ask a confirmatory question when the subject is not responsive or gives an irrelevant response (e.g., control avatar to say "Hey there!" or "Did you hear me?").

In some instances, the interface 500 may allow the supervisor to record a question (or other conversation piece) in the supervisor's voice via the supervisor's user device and transmit and playback the recorded question (or other conversation piece) to the user via the user's user device (e.g., as the police office avatar). In some instances, the interface 500 may allow the supervisor to input text, and use one or more text-to-speech converters to read the text as the police office avatar to the user. In some instances, the interface 500 may perform a speech-to-text conversion and then a text-to-speech conversion to convert the voice/tone of the supervisor in a recording. In some instances, the teaching module may be programmed, such as to execute one or more algorithms, to recognize a certain type of response from the subject and provide an automatic response without a command from the supervisor. For example, if an audio sensor (e.g., microphone) collects data from the subject's response and determines that the volume is too small, the teaching module can be programmed to have the police officer respond with "Can you say that again?" without user input from the supervisor. In such case, a supervisor can override pre-programmed responses. In another example, if an audio sensor collects data that the subject has failed to respond to a question by the police office avatar for a certain duration (e.g., 30 seconds, 1 minute, etc.), the teaching module can be programmed to have the police officer respond with "Did you hear me?" In another example, if an audio sensor collects data from the subject's response, the response can be processed via a speech-to-text conversion and compared to a model text answer. If the comparison yields a % similarity above a predetermined threshold, the teaching module can record the conversation session as a successful conversation.

In some aspects, provided are sensory-based therapies. Sensory-based therapies can include using a VR or AR environment to build specific calming or stimulating experiences with a focus on helping users with neurodevelopmental disorders or disabilities, such as autism, to manage or respond to otherwise challenging environments and situations. For example, a calming module may allow a user to play a simple and delightful musical instrument using just the direction of his or her gaze. In some instances, one or more VR or AR experiences may be designed for specific calming requirements. Such VR or AR experiences may comprise environments such as an aquarium, a beach, a butterfly park, or a play room.

Figure 6A:
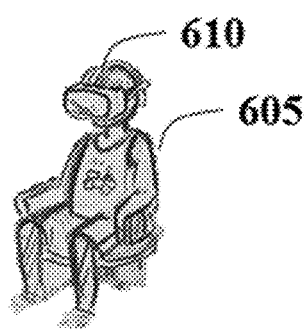
FIGS. 6A-6C illustrate a sensory module content comprising a train room.
Figure 6B:
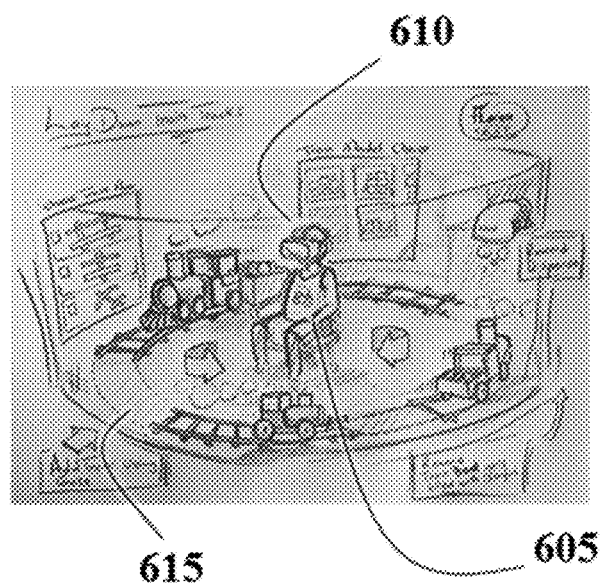
Figure 6C:
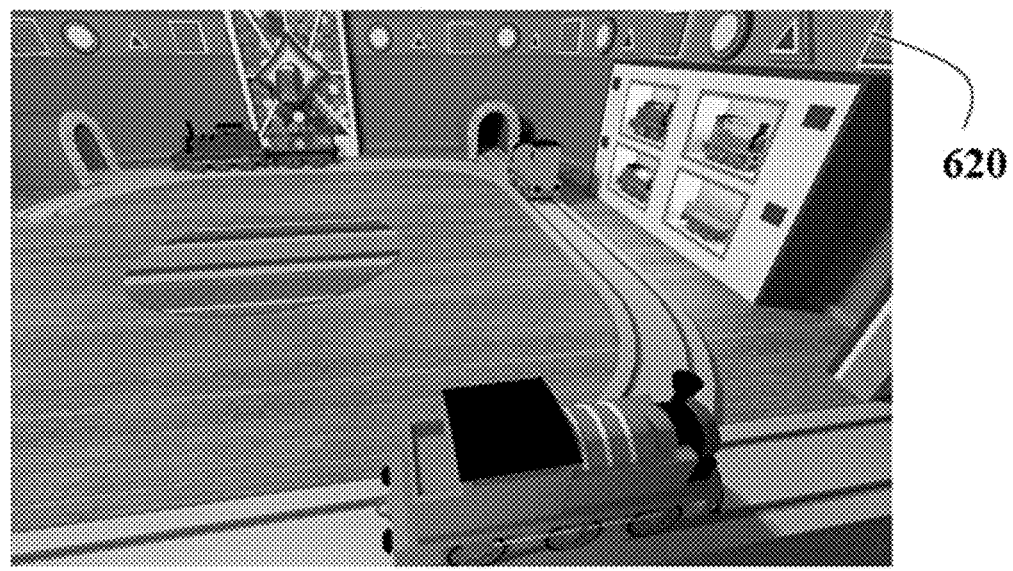

FIGS. 6A-6C illustrate a sensory module content comprising a train room. FIG. 6A shows a user 605 using a user device 610. FIG. 6B shows the user 605 using the user device 610 immersed in a virtual reality or augmented reality experience 615. FIG. 6C shows an exemplary display 620 of the sensory module as seen by the user. The sensory module comprising the train room may comprise one or more dynamic components capable of interacting with the user 605. For example, the user 605 may be capable of adding one or more train tracks using just the user's 605 gaze, receive colorful train beads as rewards, such as from a rewards dispenser, for successfully completing one or more tasks in the module (e.g., adding a train track with the user's 605 gaze), selecting a type of train track with the user's 605 gaze or other motion or output (e.g., sound, voice command, etc.), and/or selecting a train model with the user's 605 gaze or other motion or output (e.g., sound, voice, command, etc.). The train may be in animated to be in motion around the train tracks that the user 605 has built. The VR or AR experience 615 may be a 360° experience, wherein the user may view content in 360°.

Figure 6D:
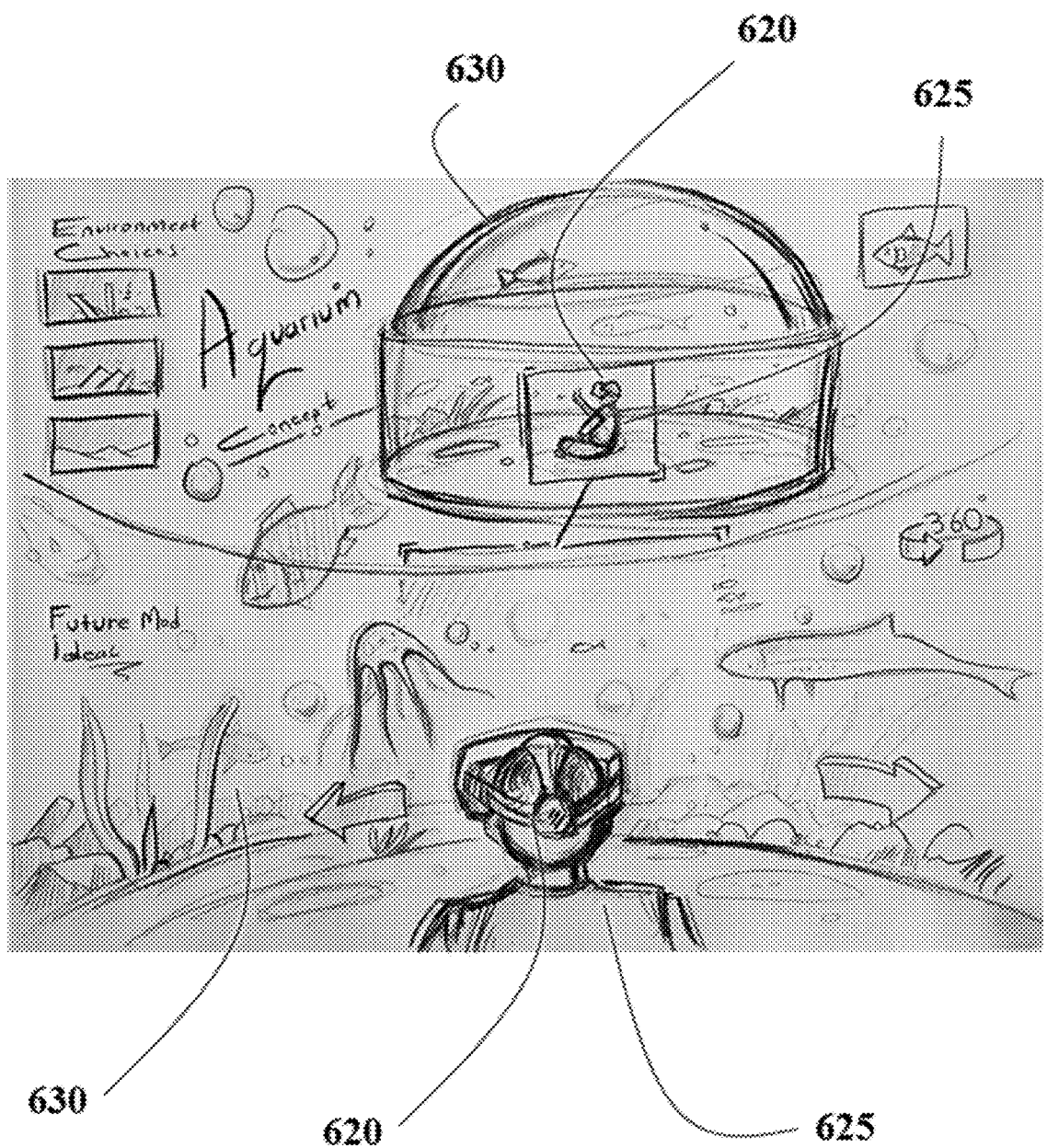
FIG. 6D illustrates a sensory module content comprising an aquarium.

FIG. 6D illustrates a sensory module content comprising an aquarium. A user 625 using a user device 620 is immersed in a virtual reality or augmented reality experience 630. The sensory module comprising the aquarium may comprise one or more dynamic components capable of interacting with the user 625. For example, the user 625 may be capable of adding one or more fish inside the aquarium using just the user's 605 gaze. The user 625 may be capable of choosing different environments. The VR or AR experience 630 may be a 360° experience, wherein the user may view content in 360°.

Figure 6E:
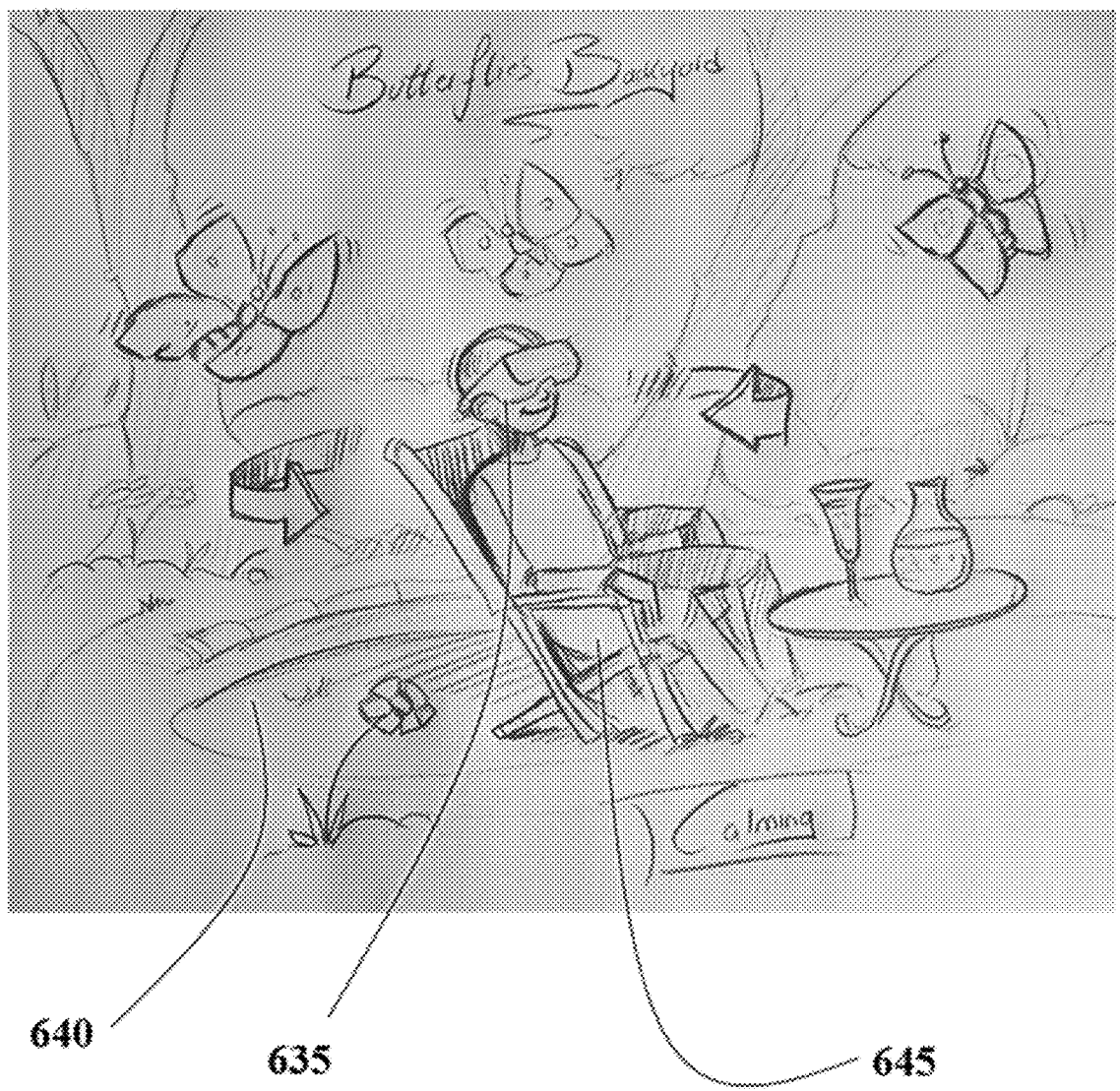
FIG. 6E illustrates a sensory module content comprising a butterfly park.

FIG. 6E illustrates a sensory module content comprising a butterfly park. A user 645 using a user device 635 is immersed in a virtual reality or augmented reality experience 640. The sensory module comprising the aquarium may comprise one or more dynamic components capable of interacting with the user 645. For example, the user 645 may be capable of adding one or more animated butterflies inside the butterfly park using just the user's 645 gaze, and/or playing a music in the background using gaze. The user 645 may be capable of choosing different environments. The VR or AR experience 640 may be a 360° experience, wherein the user may view content in 360°.

Figure 6F:
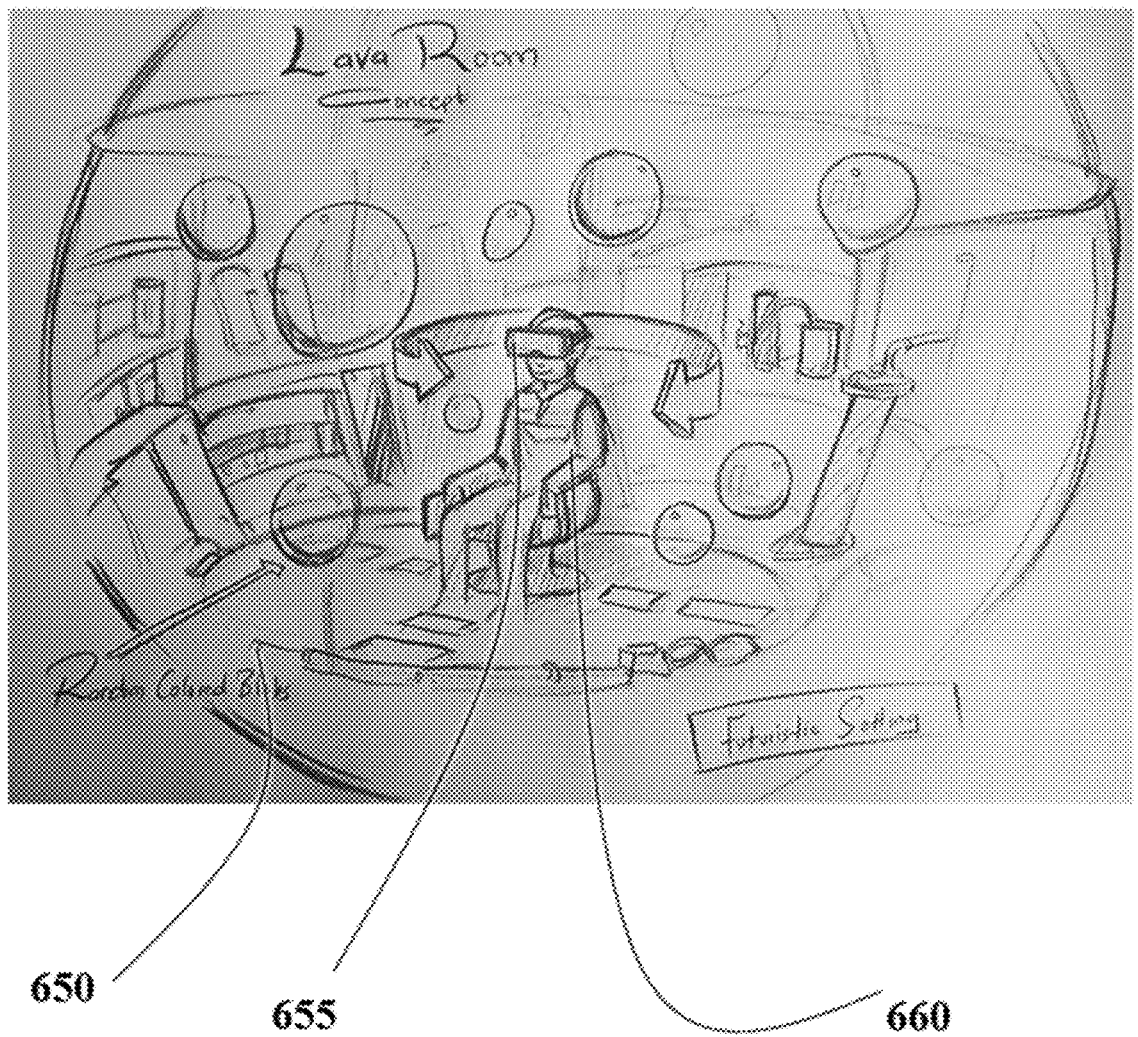
FIG. 6F illustrates a sensory module content comprising a lava room.

FIG. 6F illustrates a sensory module content comprising a lava room. A user 660 using a user device 655 is immersed in a virtual reality or augmented reality experience 650. The sensory module comprising the lava room may comprise one or more dynamic components capable of interacting with the user 660. For example, the user 660 may be capable of controlling random colored balls with just the gaze. The user 660 may be capable of choosing different environments. The VR or AR experience 650 may be a 360° experience, wherein the user may view content in 360°.

Figure 6G:
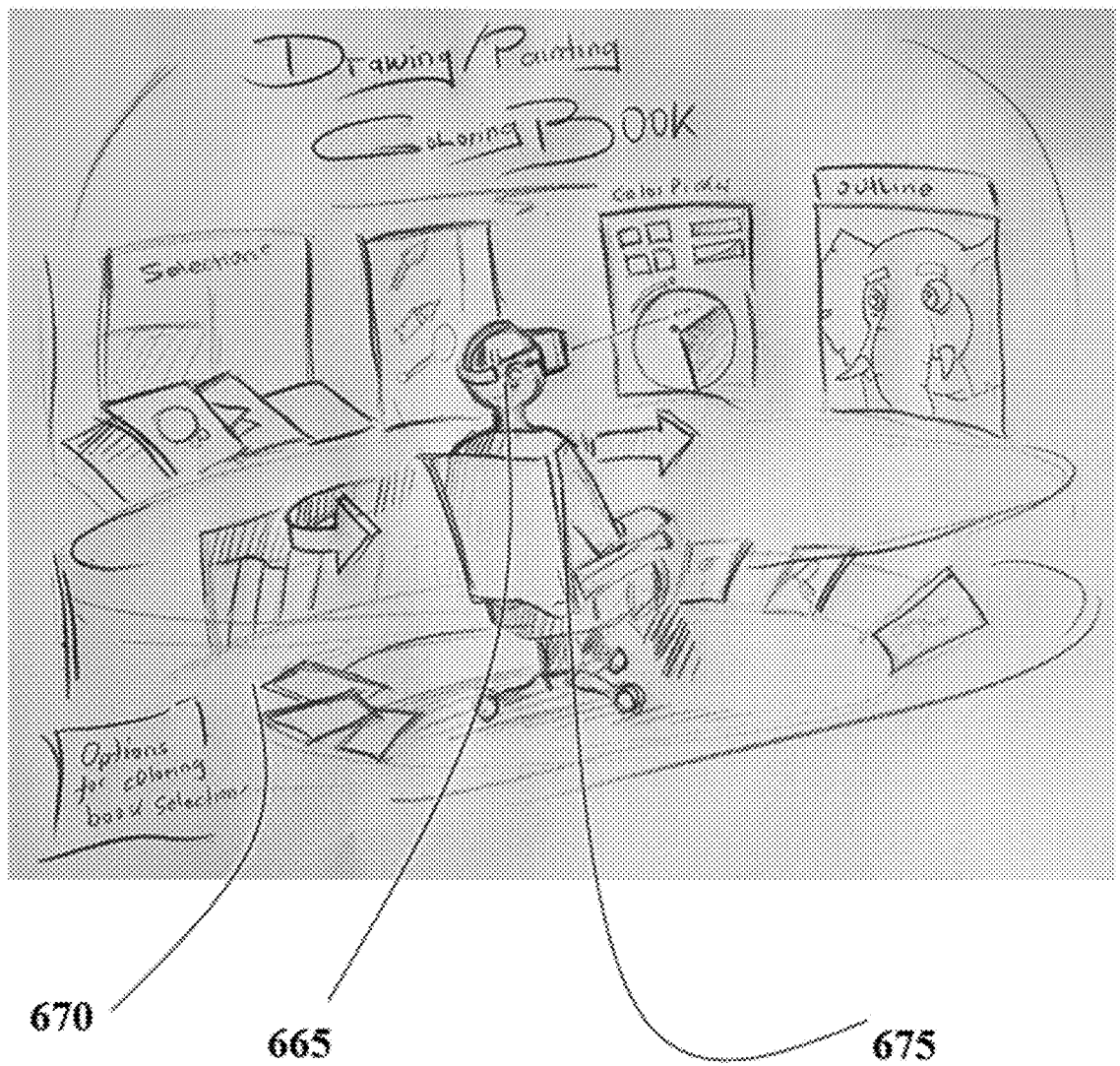
FIG. 6G illustrates a sensory module content comprising a coloring book.

FIG. 6G illustrates a sensory module content comprising a coloring book. A user 675 using a user device 665 is immersed in a virtual reality or augmented reality experience 670. The sensory module comprising the coloring book may comprise one or more dynamic components capable of interacting with the user 675. For example, the user 675 may be capable of selecting different coloring books, select different coloring outlines, color an outline with just the gaze, and/or select one or more types of pens or other tools, and parameters for the tools (e.g., width, transparency, color, etc.). The VR or AR experience 670 may be a 360° experience, wherein the user may view content in 360°.

In some aspects, provided are systems and methods for diagnosing a user with a condition. In some cases, data collected (or recorded) for one or more subjects may be aggregated to build behavior models for one or more conditions (e.g., mental or developmental disorders). Such behavior models can be leveraged as diagnostic tools for users to be evaluated through the VR or AR system. For example, a plurality of behavior models for different mental or developmental disorders can be stored in a library of behavior models, such as in one or more databases. A plurality of behavior models for each VR or AR environment, scene, or experience may be stored in a library of behavior models, such as in one or more databases. A behavior model for a first type of developmental disorder can comprise data exhibited by one or more subjects known to suffer from the first type of developmental disorder when placed in a first VR or AR environment. When a user to be diagnosed is placed in the same first VR or AR environment, or an environment similar to the first VR or AR environment, the data collected on the user may be compared to the behavior model for the first type of developmental disorder to determine whether the user has the first type of developmental disorder or not, and/or determine a degree to which the user suffers from the first type of developmental disorder. In some instances, the data collected for the user to be diagnosed may be compared to a plurality of behavior models to determine which one or more conditions the user may suffer from (and to what degree). By way of example, the higher the % similarity between the collected data for the user and the data stored for the behavior model, the more likely it is (and with higher degree) that the user suffers from the condition of the behavior model. In some instances, a user being diagnosed may be placed in a plurality of different VR or AR environments, scenes, and/or experiences (e.g., sensory calming modules, teaching modules, learning modules, etc.) and an overall performance by the user may be compared to the library of behavior models. Such comparisons may be made individually by VR or AR environments (for each type of condition) and/or by condition (for each type of VR or AR environments), and then aggregated (e.g., average, mean, median, other statistical computation or evaluation). Beneficially, the VR or AR systems may accurately and precisely diagnose a user with a condition based on comparisons of accurately measured empirical data (for example, compared to general guidelines or hunches that a child is not attentive enough), and determine a degree of intensity or progression of a condition. This may be particularly beneficial for diagnosing and treating mental or developmental disorders where it is difficult to quantify symptoms. In some instances, the diagnosis of the VR or AR systems may be implemented by one or more computer algorithms, such as machine learning algorithms, which are trained with increasing data input (e.g., more subjects, more therapy sessions using the VR or AR systems, etc.). For example, the accuracy of the diagnosis may increase as the iterations increases.

In some aspects, different virtual or augmented reality experiences may be organized in a library and be available for prescription or recommendation to care givers, parents, or the subjects themselves. For example, they may be prescribed or recommended by human experts diagnosing the subjects. Alternatively or in addition, they may be prescribed by the system via one or more computer algorithms (e.g., machine learning algorithms), such as described above. In some cases, the diagnosis, prescription, or recommendation may be made without human input. The accuracy of the diagnosis, prescription, or recommendation may increase with increasing iterations. In some instances, the virtual or augmented reality experiences and therapies can be tailored to the needs of individual subjects either manually by the human expert (e.g., therapist) or using computer algorithms. For example, the tailoring can be performed based at least on prior conditions of the subject and/or based on data collected throughout the subject's and others' use of the VR or AR system, such as described above.

The VR or AR system described herein may provide a low cost and accessible therapeutic solution for subjects who have a mental or developmental disorder. Alternatively or in addition, the VR or AR system described herein may provide educational and/or entertainment value to subjects who have a mental or developmental disorder, and subjects who do not.

Control Systems

Figure 8:
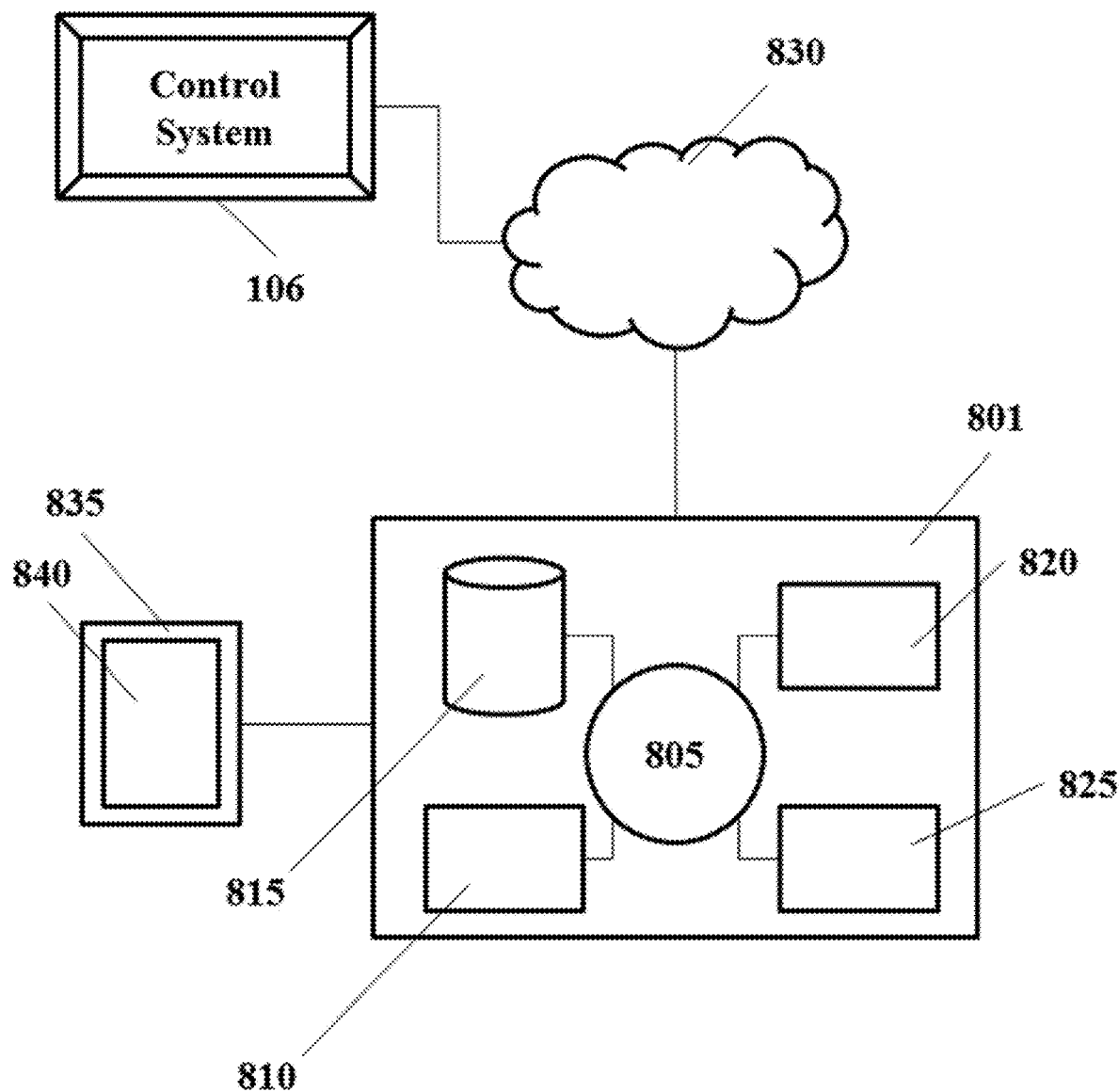
FIG. 8 shows a computer control system that is programmed or otherwise configured to implement methods provided herein.

The present disclosure provides computer control systems that are programmed to implement methods of the disclosure. FIG. 8 shows a computer system 801 that is programmed or otherwise configured to operate and display a virtual reality or augmented reality environment with or without the use of supplemental headsets or gear, execute algorithms within the virtual reality or augmented reality platform or a companion application to the virtual reality or augmented reality platform, track, save, and analyze a user's behaviors and responses in a VR or AR environment, and execute and pair a companion application that may allow a supervising user to monitor and control in real-time a user's virtual reality or augmented reality experience on a second, third, or $n^{th}$ display screen. The computer system 801 can be an electronic device of a user or a computer system that is remotely located with respect to the electronic device. The electronic device can be a mobile electronic device. The computer system 801 may be used to treat a neurodegenerative disorder, such as, for example, autism. The computer system 601 may communicate with the control system 106 of FIG. 1. In some cases, the control system 106 may comprise the computer system 801.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., VR or AR user, supervisor, therapist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, images or videos used to simulate an augmented or virtual reality experience to the user, a mobile companion application to the supervisor, or an in-room monitor to therapists. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, track a user's activity, including voice, motion, and gaze within the virtual reality or augmented reality environment, run analytics on metrics collected from a user's experience, provide therapeutic learning by iterating training principles with varying levels of difficulty, and translate commands from a paired control device.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for diagnosing a user with a mental or developmental condition, comprising:
    (a) providing a first user having a first mental or developmental condition a virtual or augmented experience, wherein the virtual or augmented experience provides one or more of a visual, auditory, and haptic stimulation to the first user;
    (b) generating a first set of sensory data of the first user in response to the one or more of the visual, auditory, and haptic stimulation;
    (c) associating the first set of sensory data to the first mental or developmental condition;
    (d) providing a second user the virtual or augmented experience;
    (e) generating a second set of sensory data of the second user in response to the one or more of the visual, auditory, and haptic stimulation; and
    (f) processing the second set of sensory data to the first set of sensory data to diagnose the second user with the first mental or developmental condition or lack thereof.

2. The method of claim 1, wherein (f) comprises diagnosing the second user with a degree to which the second user suffers from the first mental or developmental condition.

3. The method of claim 1, wherein (f) comprises determining a % similarity between the first set of sensory data and the second set of sensory data.

4. The method of claim 1, further comprising:
    in (a), providing a plurality of users each having the first mental or developmental condition, including the first user and not including the second user, the virtual or augmented experience;
    in (b), generating an aggregate data set of the plurality of users in response to the one or more of the visual, auditory, and haptic stimulation in the virtual or augmented experience, wherein the aggregate data set comprises, or is based at least in part on, said first set of sensory data;
    in (c), associating the aggregate data set to the first mental or developmental condition; and
    in (f), processing the second set of sensory data to the aggregate data set to diagnose the second user with the first mental or developmental condition or lack thereof.

5. The method of claim 1, further comprising:
    (g) providing a third user having a second mental or developmental condition the virtual or augmented experience, wherein the second mental or developmental condition is different from the first mental or developmental condition;
(h) generating a third set of sensory data of the third user in response to the one or more of the visual, auditory, and haptic stimulation;
(i) associating the third set of sensory data to the third mental or developmental condition; and
(j) processing the second set of sensory data to the third set of sensory data to diagnose the second user with the second mental or developmental condition or lack thereof.

6. The method of claim 1, wherein the virtual or augmented experience permits the first user to interact with a therapist, parent, or peer.

7. The method of claim 6, wherein the therapist, parent, or peer is located remote from the first user.

8. The method of claim 6, wherein the one or more of the visual, auditory, and haptic stimulation is provided or instructed by the therapist, parent or peer.

9. The method of claim 1, further comprising:
in (a), providing the first user with a second virtual or augmented experience, wherein the second virtual or augmented experience provides one or more of a second visual, auditory, and haptic stimulation to the first user;
in (b), generating an aggregate data set from (i) the first set of sensory data of the first user in response to the one or more of visual, auditory, and haptic stimulation in the virtual or augmented experience, and (ii) a third set of sensory data of the first user in response to the one or more of the second visual, auditory, and haptic stimulation in the second virtual or augmented experience;
in (c), associating the aggregate data set to the first mental or developmental condition;
in (d), further providing the second user the second virtual or augmented experience;
in (e), generating a second aggregate data set from (i) the second set of sensory data of the second user in response to the one or more of visual, auditory, and haptic stimulation in the virtual or augmented experience, and (ii) a fourth set of sensory data of the second user in response to the one or more of the second visual, auditory, and haptic stimulation in the second virtual or augmented experience
in (f), processing the second aggregate data set to the aggregate data set to diagnose the second user with the first mental or developmental condition or lack thereof.

10. A method for diagnosing a user with a mental or developmental condition, comprising:
(a) providing a first user with one or more virtual or augmented experiences, wherein the one or more virtual or augmented experiences is configured to provide the first user one or more of a visual, auditory, and haptic stimulation to the first user;
(b) generating a first set of sensory data of the first user in response to the one or more of the visual, auditory, and haptic stimulation in the one or more virtual or augmented experiences; and
(c) processing the first set of sensory data of the first user to one or more behavior models in a library of behavior models, wherein a behavior model of the one or more behavior models is associated with (i) a mental or developmental condition and (ii) the one or more virtual or augmented experiences, to diagnose the first user with the mental or developmental condition or lack thereof.

11. The method of claim 10, wherein the behavior model is generated from sensory data collected from a second user having the mental or developmental condition in response to the one or more of the visual, auditory, and haptic stimulation provided to the second user in the one or more virtual or augmented experiences.

12. The method of claim 11, wherein the behavior model is generated from sensory data collected from a plurality of users, including the second user and not including the first user, each having the mental or developmental condition, in response to the one or more of the visual, auditory, and haptic stimulation provided to the plurality of users in the one or more virtual or augmented experiences.

13. The method of claim 10, wherein (c) comprises diagnosing the first user with a degree to which the first user suffers from the mental or developmental condition.

14. The method of claim 10, wherein (c) comprises determining a % similarity between the first set of sensory data and a set of sensory data associated with the behavior model.

15. The method of claim 10, wherein the one or more virtual or augmented experiences permit the first user to interact with a therapist, parent, or peer.

16. The method of claim 15, wherein the therapist, parent, or peer is located remote from the first user.

17. The method of claim 15, wherein the one or more of the visual, auditory, and haptic stimulation is provided or instructed by the therapist, parent or peer.

18. The method of claim 10, wherein each behavior model in the library of behavior models is associated with (i) a given mental or developmental condition and (ii) a given one or more virtual or augmented experiences.

19. The method of claim 10, wherein the behavior model is further associated with (i) a second mental or developmental condition different from the mental or developmental condition, (ii) an additional virtual or augmented experience in addition to the one or more virtual or augmented experiences, or both.

20. The method of claim 10, wherein (c) comprises processing the first set of sensory data of the first user to the one or more behavior models in the library of behavior models to diagnose the first user with a plurality of different types of mental or developmental conditions, including the mental or developmental condition, or lack thereof.

* * * * *